(12) United States Patent
Huang

(10) Patent No.: US 8,318,494 B2
(45) Date of Patent: Nov. 27, 2012

(54) GENETIC MATERIAL AND CHROMOSOMAL PROCESSING AND MANIPULATION METHODS

(75) Inventor: Yaoxiong Huang, GuangZhou (CN)

(73) Assignee: Geneforge Limited, Hong Kong (HK)

( * ) Notice: Subject to any disclaimer, the term of this patent is extended or adjusted under 35 U.S.C. 154(b) by 286 days.

(21) Appl. No.: 12/622,427

(22) Filed: Nov. 19, 2009

(65) Prior Publication Data

US 2011/0159591 A1 Jun. 30, 2011

(51) Int. Cl.
*C12N 15/87* (2006.01)
*B23K 15/00* (2006.01)

(52) U.S. Cl. .... 435/446; 435/455; 435/460; 219/121.14

(58) Field of Classification Search .................. None
See application file for complete search history.

(56) References Cited

U.S. PATENT DOCUMENTS 5,713,891 A * 2/1998 Poppas ............................. 606/2

FOREIGN PATENT DOCUMENTS

WO     WO9638093 A1   12/1996
WO     WO2004/053082 A2 * 6/2004

OTHER PUBLICATIONS

Vorobjev et al (Biophysical Journal. 1993. 64:533-538).*
Seeger et al. (Cytometry. 1991; 12: 497-504).*
Rabau, Micha Y. et al., Healing Process of Laser-Welded Intestinal Anastomosis, Lasers in Surgery and Medicine, Dec. 31, 1994, vol. 14, No. 1, pp. 13-17, ISSN 0196-8092, abstract provided cited in International Search Report as 'A' reference related to general state of the art but not considered to be of particular relevance.

* cited by examiner

*Primary Examiner* — Scott Long
(74) *Attorney, Agent, or Firm* — James Christopher Schroeder

(57) ABSTRACT

The presently claimed invention applies to a genetic material processing and manipulation method and related product. The claimed invention relates to a method for changing the inherited characteristics of a cell through chromosome processing treatment. In a preferred embodiment, 'genomic surgery' is applied to source genetic material 101. Micro-beam cutting takes place on target genetic material 103, which is moved by way of micro-beam transport to a destination location adjacent to desired target genetic material 105. Source and target genetic material are welded during a micro-beam welding step, resulting in a combined or new chromosome combination 125. The combined or new chromosome combination 125 is transferred into receptor cell by three ways. The presently claimed invention provides a high quality alternate approach to directed genetic recombination without requiring the use of restriction enzymes and is used for chromosomal repair, removal of defects and new organism creation.

19 Claims, 2 Drawing Sheets

GENETIC MATERIAL AND CHROMOSOMAL PROCESSING AND MANIPULATION METHODS

CROSS REFERENCE TO RELATED APPLICATIONS

This application claims priority to China Application Number 200810219234X filed on Nov. 19, 2008 and to PCT application No. PCT/CN2009/074998 filed Nov. 17, 2009.

BACKGROUND OF INVENTION

1. Technical Field

The claimed invention is related to genetic technology, particularly involving the process of genetic material and chromosomal processing and manipulation.

2. Description of Related Art

Known methods exist for DNA manipulation, but the current methods have inherent limitations. Target site samples must be prepared before cutting with restriction enzymes. Because each type of restriction enzyme only recognizes a specific nucleotide sequence, and only in a specific site on cleaved DNA, use of this technology has substantial limitations.

Another method currently in use is the micro-cell-mediated chromosome transfer (MMCT) method. The MMCT technique requires that the donor cells are treated with colchicine amines. The cytochalasin B treatment is used on one or a few chromosomes containing microcapsules, and then microencapsulated with the receptor cell by fusion, thus transferring the microcapsules with the chromosome into the inside of the cell. A similar approach is used for cellular disassociation as well.

These techniques have a number of challenges including difficulties to control and access target chromosomes, as well as the inability to repair or remove defective chromosomes. As a consequence, alternate approaches to genetic material micromanipulation are desirable.

BRIEF SUMMARY OF THE INVENTION

According to the presently claimed invention, a novel method of chromosomal manipulation and modification is hereby disclosed. By applying micro-beam techniques, chromosomes are cut and manipulated to a very fine degree of control. Although laser ablation has been used on genetic material to a limited degree, the previously implemented techniques lack refinement and specificity. Moreover, the limited attempts at using lasers on chromosomal materials have not included directed chromosomal modification to bring about the desired addition, repair or deletion of genetic material.

Through the use of the presently claimed invention, genetic material is modified so that living cells are modified to resume their normal life activities and functions. Moreover, in particular embodiments, desired chromosomes, chromosome fragments, or modified genetic material of exogenous origin are introduced into cells so that new genes are expressed and with cell division the newly introduced traits are passed to progeny cells.

A primary objective of the presently claimed invention is to overcome the shortcomings and deficiencies of existing technologies to enable modification of genetic material without requiring the use of restriction enzymes. As a direct and intended consequence, chromosomes are modified at a desired location rather than limited to the site specificity of a particular restriction enzyme.

In a primary embodiment of the presently claimed invention, genetic material is processed and manipulated to effect a desired chromosomal change by utilizing one or more of the following steps:

(1) Chromosome Cutting: By using a micro-beam, selected parts of chromosomes are cut. While the focus of the beam will vary depending on the physical characteristics and thickness of the genetic material cut, in a preferred embodiment an energy density of $10 \times 10^6$ J/m$^2$~$400 \times 10^6$ J/m$^2$ is desirable. In a preferred embodiment the cuts made are either along a straight line or a curved line. The cutting process is repeated on a particular target site as needed.

(2) Chromosome Moving: After cutting, optical tweezers are used to transfer the chromosome or fragment of genetic material to the desired location. According to the size of chromosome transfer, in preferred embodiments the beam will utilize a power density of $10 \times 10^9$ W/m$^2$~$200 \times 10^9$ W/m$^2$.

(3) Chromosome Welding: After chromosome cutting or chromosome moving (in particular desired embodiments the welding can be performed with two chromosomes without cutting), the two adjacent pieces of genetic material are ready for joining by way of chromosome welding. When employing a butt welding technique in a preferred embodiment, the micro-beam utilizes an energy density of $5 \times 10^5$ J/m$^2$~$200 \times 10^6$ J/m$^2$ with an exposure time of 1~80 seconds, depending on the micro-beam used in the power density to create a new genetic material composition.

(4) Genetic Composition Transfer: After chromosome moving, cutting or welding, the genetic material in particular embodiments may be transferred to a target cell. Alternate transfer methods include a first method, where a micro-beam with an energy density of $10 \times 10^6$ J/m$^2$~$400 \times 10^6$ J/m$^2$ perforates a hole in the receptor cell, and then uses a power density of $10 \times 10^9$ W/m$^2$~$200 \times 10^9$ W/m$^2$ micro-beam backdrop to move the genetic composition through the hole and into the receptor cell.

An alternate second method begins with the first method then uses micro-tube manipulation control technology to select the chromosome or genetic material by inhalation via microtubules, then injects the chromosome or genetic material into the desired receptor cell through the hole made up by the micro-beam. An alternate embodiment includes directly inserts the microtubule into the desired receptor cell then injects the genetic composition.

In a preferred embodiment of chromosome processing and manipulation, the micro-beam has a diameter of 0.6~3 microns and a wavelength in the range of 193 nm~2940 nm. Depending on the wavelength selected, the micro-beam is used to either cut, move or weld a target sample. In a preferred embodiment, micro-manipulation is carried out by way of microtubules with an internal diameter of 0.2~100 microns. The micro-tubes capture small objects or liquids for inhalation by applying a negative pressure or injection micro-manipulation by applying a positive pressure. While the methods are described for use with chromosomes, it is an express intent of the claimed invention that any sort of genetic material can be manipulated according to the claimed methods, and not limited to genetic material or chromosomes of humans but also include all kind of animals, plants and micro-chromosomal fragments.

Applications for the claimed invention include chromosomal processing and manipulation to change the genetic characteristics of cells. As a result, chromosome pairs can be repaired and defective chromosomes are removed or repaired.

By micro-beam processing and manipulation of the genetic material genetic defects can be corrected so that the living organism can begin healthy expression of the proper gene product. The creation of new organisms is also hereby made possible.

A principle objective of an embodiment of the claimed invention is as follows. Non-mechanical contact is made with a target specimen by utilizing a micro-beam. The micro-beam acts as optical tweezers to apply a force to suspend, flip, transport and manipulate the target specimen. By changing the wave length and power density, the micro-beam also uses photo-thermal effects or photochemical processes to carry out micro-cutting, perforation as well as micro-welding on the target materials. Since the micro-beam can be focused to micron size, very fine cutting, perforation and welding is enabled. Additional embodiments include computer controlled electro-optical processes for flexibility and convenience.

The presently claimed invention relative to existing technology has the following advantages and beneficial effects:

(1) Micro-beam processing and manipulation applied to genetic material enables greatly enhances chromosomal modifications. Benefits include genetic material cutting, transport, welding and insertion into receptor cells by direct guidance. Precision is combined with speed and ease of use.

(2) Restriction enzymes are not required for cutting or connection of genetic material, greatly simplifying the processing steps, increasing ease of target handling and reducing overall processing costs.

(3) Genetic material manipulation and chromosome modifications are carried out with only micro-beam technology, and as a result mechanical contact is not required for chromosomal manipulation, so that the processed chromosome can retain its structure and condition without any mechanical damage.

(4) The claimed method is used to correct, supplement or repair the chromosome, as well as exogenous chromosome or chromosome segment transfer to receptor cells to change cell genetic characteristics for a wider range of applications.

Illustrative terms such as chromosome are used throughout the application with the intent that the claimed invention is equally applicable to a wide variety of genetic material. Furthermore, references to techniques such as optical tweezers should be readily apparent to one skilled in the art to include obvious and equally applicable variants. With respect to the use of a micro-beam, in main embodiments the micro-beam is electromagnetic radiation. Foreseeable variants include the use of electromagnetic radiation which includes ultraviolet, visible light, infrared and microwave radiation.

BRIEF DESCRIPTION OF THE SEVERAL VIEWS OF THE DRAWING

FIG. 1 is the application of the presently claimed invention by microscopic view of the process as applied to *Drosophila* chromosomes (circle part indicating the treatment of the target area), of which:

FIG. 1 (*a*) shows fruit fly chromosomes;

FIG. 1 (*b*) shows a *Drosophila* chromosome fragment being cut by micro-beam;

FIG. 1 (*c*) shows the cut chromosome fragment being captured by another micro-beam;

FIG. 1 (*d*) shows the fragment being transferred by micro-beam to the vicinity of another chromosome;

FIG. 1 (*e*) shows the fragment being positioned with another chromosome for welding;

FIG. 1 (*f*) shows the welding of the two fragments by micro-beam.

DETAILED DESCRIPTION OF A PREFERRED EMBODIMENT

The following examples and drawings depict an implementation of the presently claimed invention in further detail.

Figure 1:
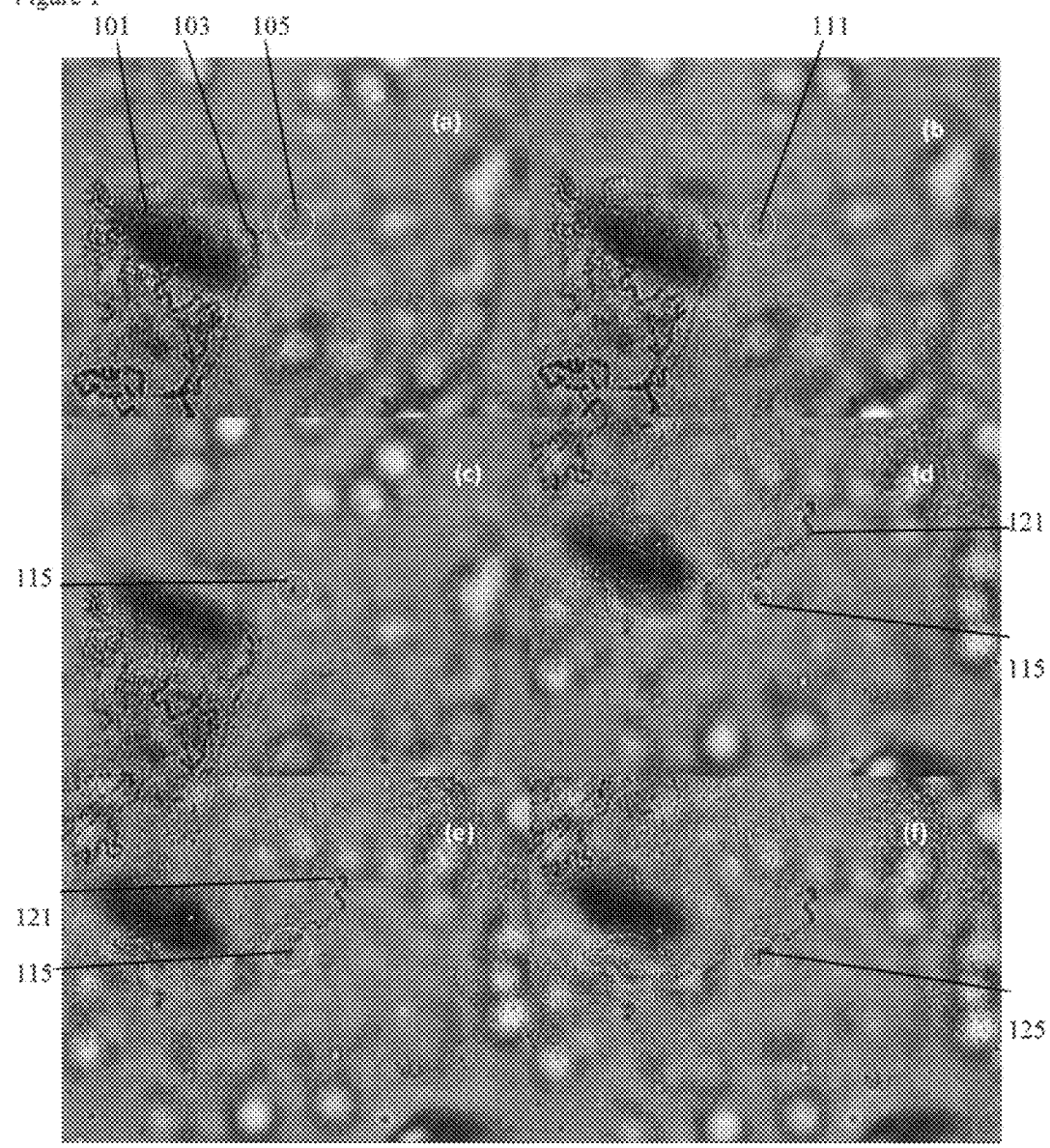

In a first illustrative example:

Preparation step one prepares samples of *Drosophila* salivary gland chromosomes by placing *Drosophila* third instar larvae salivary glands (not shown) on a glass slide (not shown) and dissociated with 1 mol/L hydrochloric acid (not shown). After one minute the hydrochloric acid is removed with a dropper (not shown) and the samples are washed with distilled water three times. After the final washing the sample gland cells are left in distilled water (not shown) for 20 minutes, so that salivary gland cells are allowed to undergo full water-swelling so that the target chromosomes disperse;

Cutting step two is illustrated by FIG. 1(*a*) which shows sample (101) containing chromosomes (103, 105) prepared for cutting. Sample (101) is placed in an inverted microscope stage (not shown). Using a wavelength of 337 nm; the pulsed nitrogen laser beam is focused through the microscope objective to a micro-beam of 1 micron in diameter. The energy density of the beam is adjusted to $168 \times 10^6$ J/m². FIG. 1(*b*) depicts chromosome alignment and cutting at the site of exposure (111).

Positioning step three is illustrated by FIG. 1(*c*) and FIG. 1(*d*) where laser irradiation used for cutting is turned off and another laser with wavelength of 1064 nm from a continuous single-mode Nd: YAG laser is introduced into the microscope. The Nd: YAG laser is focused to a micro-beam with a diameter of 1 micron by the objective of the microscope, so its power density is $63 \times 10^9$ W/m² when its output power is adjusted to 50 mW and acts as optical tweezers. Through the use of the optical tweezers the cut down chromosome segment (115) is captured, and then moved close to the second chromosome (121). FIG. 1(*e*) depicts the positioning and alignment of the fragment (115) for contact with the second chromosome (121).

Welding step four is illustrated by FIG. 1(*f*) where a wavelength of 337 nm pulsed nitrogen laser beam (not shown) is focused through a microscope objective (not shown) into a micro-beam of 1 micron in diameter. In the illustrative example, the beam's energy density is adjusted to $152 \times 10^6$ J/m². The two chromosomes are radiated with the light beam for 18 seconds, after which the two chromosomes are firmly welded to one (125).

Relocation step five uses a laser beam with a wavelength of 337 nm and an energy density of $210 \times 10^6$ J/m² to perforate a hole (not shown) on receptor cell (not shown). Micro-tube control technology is then applied to carry the welded chromosome through the micro-pore into the receptor cell then injects the welded chromosome segment by injection.

In a second illustrative example:

Preparation step one prepares chromosome samples of human lymphocyte by obtaining a small amount of peripheral blood, followed by culturing the cells for 72 hours in a short-term culture into the proliferative phase, when the accession of colchicine inhibits cell division, so that cell division stops in the middle phase to get an adequate amount of division-phase cells. A hypotonic treatment is applied to collect the cells during which the cells swell with chromosome stretching. Remnant proteins of mid phase are removed so that chromosomes are clear with good dispersion.

During cutting step two the sample is placed in an inverted microscope, and the chromosomes to be cut is positioned in the field of view. In the illustrative example, a 337 nm wavelength pulsed nitrogen laser beam is focused through the microscope objective to a micro-beam of 1 micron in diameter. The beam's energy density is adjusted to $127 \times 10^6$ J/m² and chromosome is aligned and cut down at the site of exposure to create a smaller fragment and the laser beam is stopped.

Positioning step three occurs by directing a 1064 nm wavelength continuous single-mode Nd:YAG laser into the microscope, and focusing through the microscope objective to create a micro-beam of 1 micron in diameter with a $51 \times 10^9$ W/m² power density. By use of the optical tweezers effect the cut down chromosome segment is captured and moved close to the second chromosome. The chromosome fragment and second chromosome segment are aligned together to prepare for welding.

Welding step four occurs by routing a 337 nm wavelength pulsed nitrogen laser beam through the microscope objective to become a micro-beam of 1 micron in diameter. In the illustrative embodiment, the beam's energy density is adjusted to $102 \times 10^6$ J/m². The two chromosomes are targeted for welding at the exposure site for 10 seconds, so that the two chromosomes are joined in a solid weld.

Relocation step five occurs by using a laser micro-beam with a wavelength of 337 nm and an energy density of $250 \times 10^6$ J/m² to perforate a hole in the desired receptor cell. By transitioning the laser wavelength to 1064 nm with $80 \times 10^9$ W/m² power density, the welded chromosome is moved by the optical tweezers into the hole of the receptor cell.

In a third illustrative example:

Preparation step one prepares chromosome samples of garlic. A robust garlic root tip is selected and placed in a petri dish along with 0.2% colchicine aqueous solution at room temperature for 2 hours. The root tip is treated with 0.075 mol/L of KCl hypotonic solution for 20 min, and then washed with distilled water two times. After washing, the tip is placed in 2.5% cellulase and 2.5% of the equivalent mixture of pectinase (PH5.0-5.5) at 25° C. for 2-2.5 hours for dissociation or optionally placed in 60° C. water bath for 15 min, when the apical elongation zone becomes transparent and the meristematic zone is beige. After washing by distilled water the sample is pre-cooled and placed on a glass slide where 1-2MM of the root cap meristematic zone is fixed and heated at 70° C.-80° C.

During cutting step two the sample is placed on the stage of an inverted microscope, bringing the target chromosomes within the microscope field of view. A 337 nm wavelength pulsed nitrogen laser is focused through the microscope objective into a micro-beam with 1 micron diameter. The energy density of the micro-beam is adjusted to $159 \times 10^6$ J/m². The target chromosome is then aligned and cut at the exposure site and the laser beam is turned off.

Positioning step three takes place by using a 1064 nm wavelength continuous single-mode Nd:YAG laser directed into the microscope, focusing the beam through the microscope objective into 1 micron in diameter with a $66 \times 10^9$ W/m² power density. By use of the optical tweezers effect the cut down chromosome segment is captured, and then moved close to the second chromosome. Chromosome alignment takes place in preparation for joining.

Welding step four takes place by using a 337 nm wavelength pulsed nitrogen laser focused through the microscope objective into a micro-beam of 1 micron in diameter. The energy density is adjusted to $160 \times 10^6$ J/m². The two chromosomes are targeted at the welding site and exposed to the micro-beam for 7 seconds, so that the two chromosome fragments are joined in a solid weld.

Relocation step five is carried out by using a micro beam with a 337 nm wavelength and a $320 \times 10^6$ J/m² energy density. The micro-beam perforates a selected hole on the receptor cell, and with micro-tube control technology the welded chromosome composition is captured by suction and injected through the micro-pore into the receptor cell.

Figure 2:
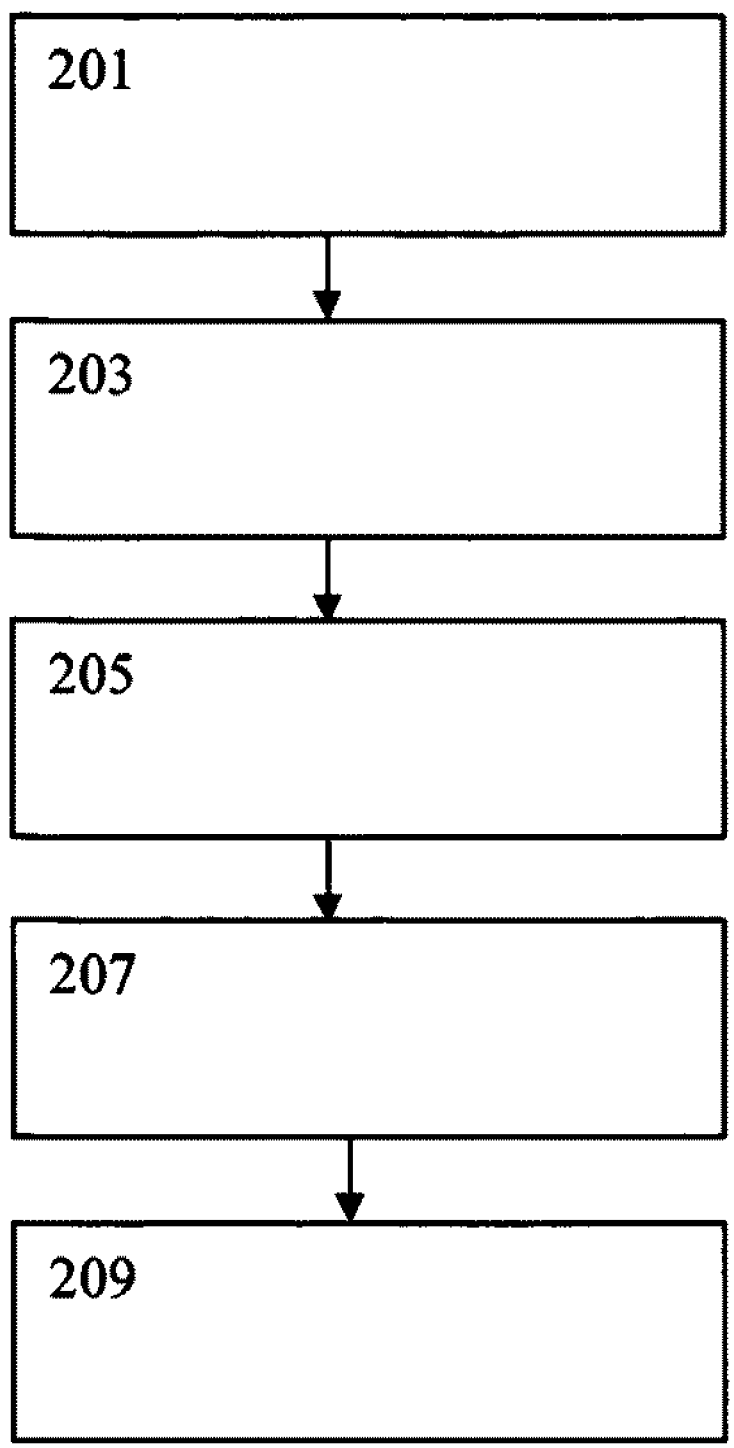
FIG. 2 is a flow diagram according to the claimed invention.

FIG. 2 is a flow diagram according to the claimed invention. Sample preparation step 201 is followed by cutting step 203. Positioning step 205 positions the genetic material fragments (not shown) for joining during welding step 207. After welding, the newly joined genetic material composition can optionally be inserted into a target cell (not shown) by repositioning step 209.

The illustrated examples depict selected ways to implement the presently claimed invention, but the presently claimed invention may also be applied in a manner not covered by the above-mentioned cases. The examples are provided by way of illustration and not by restriction of the implementation of the claimed invention. Other approaches may also be applied which do not deviate from the essence and spirit of the presently claimed invention. Foreseeable changes, modifications, substitutions, combinations or simplifications can be applied as equivalent methods and are included in the presently claimed invention within the scope of protection.

I claim:

1. A genetic recombination method, comprising the steps of:
    acquiring cut source genetic material,
    transporting source genetic material to a target location adjacent to target genetic material, and
    micro-beam welding said source genetic material to said target genetic material to create combined genetic material.

2. The method of claim 1 wherein the micro-beam welding step applies electromagnetic radiation with wavelength from the ultraviolet to the infrared spectrum.

3. The method of claim 1 wherein the micro-beam welding step takes place at a wavelength in the range of 193 nm~2940 nm.

4. The method of claim 3 wherein the micro-beam welding step utilizes an energy density of $5 \times 10^5$ J/m²~$200 \times 10^6$ J/m².

5. The method of claim 4 wherein the micro-beam welding step has an exposure time of 1~80 seconds.

6. The method of claim 2 wherein the micro-beam welding step takes place within a destination receptor cell.

7. A genetic recombination method, comprising the steps of:
    acquiring source genetic material,
    transporting source genetic material to a target location adjacent to target genetic material, and
    micro-beam welding said source genetic material to said target genetic material to create combined genetic material wherein the micro-beam welding step takes place outside the receptor cell.

8. The method of claim 3 wherein the micro-beam has a beam diameter of 0.6~3 microns.

9. The method of claim 1 wherein the transporting step moves said source genetic material utilizing micro-beam transportation.

10. The method of claim 9 wherein the micro-beam transportation step applies electromagnetic radiation with wavelength from the ultraviolet to the infrared spectrum.

11. The method of claim 9 wherein the micro-beam transportation step takes place at a wavelength in the range of 193 nm~2940 nm.

12. The method of claim 11 wherein the micro-beam transportation step has a beam diameter of 0.6~3 microns.

13. The method of claim 9 wherein the transporting step is carried out by micro-beam with power density of $10\times10^9$ W/m$^2$~$200\times10^9$ W/m$^2$.

14. A genetic recombination method, comprising the steps of:
  acquiring source genetic material,
  transporting source genetic material to a target location adjacent to target genetic material, and
  micro-beam welding said source genetic material to said target genetic material to create combined genetic material wherein the micro-beam welding step additionally comprises a transfer step to transfer the combined genetic material into receptor cell.

15. The method of claim 14 wherein a micro-beam is focused on a receptor cell to perforate a hole, followed by a micro-manipulation step wherein a micro tube is used to direct and inject the combined genetic material into the receptor cell through the hole of the cell.

16. The method of claim 15 wherein the transfer step takes place using an energy density of $10\times10^6$ J/m$^2$~$400\times10^6$ J/m$^2$ to perforate a hole on a receptor cell.

17. The method of claim 15 wherein the micro-manipulation step takes place using power density of $10\times10^9$ W/m$^2$~$200\times10^9$ W/m$^2$ to transfer the combined genetic material.

18. The method of claim 14 wherein the transfer step directly inserts the micro-tube into the receptor cell to inject the combined genetic material.

19. A genetic recombination method, comprising the steps of:
  acquiring exogenous source genetic material,
  transporting source genetic material to a target location adjacent to target genetic material, and
  micro-beam welding said source genetic material to said target genetic material to create combined genetic material.

* * * * *